United States Patent [19]

Monsan et al.

[11] Patent Number: 5,348,863
[45] Date of Patent: Sep. 20, 1994

[54] PROCESS FOR THE ENZYMATIC PREPARATION OF BASIC FIBROBLAST GROWTH FACTOR

[75] Inventors: Pierre Monsan, Mondonville; Francois Paul; Didier Betbeder, both of Toulouse, all of France; Paolo Sarmientos, Milan, Italy

[73] Assignee: Farmitalia Carlo Erba S.R.L., Milan, Italy

[21] Appl. No.: 842,177

[22] PCT Filed: Jul. 30, 1991

[86] PCT No.: PCT/EP91/01428
§ 371 Date: Apr. 2, 1992
§ 102(e) Date: Apr. 2, 1992

[87] PCT Pub. No.: WO92/02539
PCT Pub. Date: Feb. 20, 1992

[30] Foreign Application Priority Data

Aug. 2, 1990 [GB] United Kingdom ............... 9017008

[51] Int. Cl.$^5$ .............. C12P 21/00; A61K 37/36; C07K 3/10; C07K 13/00
[52] U.S. Cl. ................... 435/68.1; 530/399; 530/413
[58] Field of Search ............... 435/68.1; 530/399, 413

[56] References Cited

U.S. PATENT DOCUMENTS

| | | | |
|---|---|---|---|
| 4,785,079 | 11/1988 | Gospodarowicz et al. | 530/399 |
| 4,956,455 | 9/1990 | Esch et al. | 530/399 |
| 5,026,839 | 6/1991 | Moscatelli et al. | 536/27 |
| 5,136,025 | 8/1992 | Scheuermann et al. | 530/413 |

FOREIGN PATENT DOCUMENTS 3253689 10/1989 Australia .
0337264 10/1989 European Pat. Off. .

OTHER PUBLICATIONS

Sommer et al. (1989) *J Cell Physiol*, 138, 215–220.
Esch et al, (1985) *Proc. Nat. Acad. Sci., USA*, 82, 6507–6511.
Eriksson et al, (1991) *Proc. Nat. Acad. Sci., USA*, 88 3441–3445.
Kajio et al, (1992) *FEBS Lett.*, 306(2–3), 243–246.
Betbeder, D., "Production of Homogeneous . . . Molecular Forms", *Journal of Biotechnology*, vol. 21, No. 1,2, Nov. 1991, pp. 83–92.
Proc. Natl. Acad. Science, USA, vol. 84, Apr. 1987, Biochemistry (Washington US) M. Klagsbrun et al.: "Multiple forms of basic fibroblast growth factor: Amino-terminal cleavages by tumor cell and brain cell-derived acid proteinases", pp. 1839–1843.
Biochemical and Biophysical Research Communications, vol. 138, No. 2, Jul. 31, 1986, N. Ueno et al.:

(List continued on next page.)

Primary Examiner—Douglas W. Robinson
Assistant Examiner—Jon P. Weber
Attorney, Agent, or Firm—Oblon, Spivak, McClelland, Maier & Neustadt

[57] ABSTRACT

A bFGF is prepared by:

(i) forming an adduct between heparin or heparan sulphate and a bFGF which has the 9–10 Leu-Pro bond;

(ii) treating the adduct with pepsin A or cathepsin D, thereby cleaving the said bond; and (iii) releasing from the adduct the bFGF thus obtained.

This process may be applied to prepare the 146 amino acid form of bFGF from longer forms of bFGF. It may also be used to produce a single form of bFGF from a mixture of bFGFs whose amino acid sequences differ only by having different N-terminii.

15 Claims, No Drawings

OTHER PUBLICATIONS

"Isolation of an amino terminal extended form of basic fibroblast growth factor", pp. 580–588.

The Journal of Biological Chemistry, vol. 254, No. 15, 1979, (Baltimore, US) J. N. Whitaker et al.: "The sequential limited degradation of bovine myelin basic protein by bovine brain cathepsin D", pp. 6956–6963.

The Journal of Biological Chemistry, vol. 253, No. 10, May 25 1978 (US) D. Gospodarowicz et al.: "Purification of the fibroblast growth factor activity from bovine brain", pp. 3736–3743.

Methods in Enzymology, vol. 182, 1990, Guide to Protein Purification, Ed. by M. P. Deutscher, Academic Press, pp. 609–613.

The Journal of Biological Chemistry, vol. 263, 31, 16741–16473, 1988, Philip J. Barr, et al "Expression and Processing of Biologically Active Fibroblast Growth Factors in the Yeast Saccharomyces cerevisiae".

Journal Of Cellular Physiology 128:475–478(1986), D. Gospodarowicz, et al. "Heparin Protects Basic and Acidic FGF From Inactivation".

Analytical Biochemistry 181, 33–39 (1989)Michael Ploug, et al "Determination of Amino Acid Compositions and $NH_2$—Terminal Sequences of Peptides Electroblotted onto PVDF Membranes from Tricine—Socium Didecyl Sulfate—Polyacrylamide Gel Electrophoresis: Application to Peptide Mapping of Human Complement Component C3".

PROCESS FOR THE ENZYMATIC PREPARATION OF BASIC FIBROBLAST GROWTH FACTOR

The present invention relates to the enzymatic preparation of basic fibroblast growth factor (bFGF).

bFGF was originally isolated from brain and pituitary as a polypeptide of 146 amino acids (Esch et al, PNAS USA 82, 6507-6511, 1985). The gene for bovine bFGF has been cloned (Abraham et al, Science, 233, 545-548, 1986). The nucleotide sequence predicted a 155 amino acid bFGF translation product. Further work has shown that a 154 amino acid bFGF can be extracted together with a 146 amino acid bFGF from normal pituitary tissue upon addition of enzyme inhibitors (Ueno et al, Biochem. Biophys. Res. Comm. 138, 580-588, 1986) and that acid proteases in brain and hepatoma cells cleave bFGF (Klagsbrun et al, PNAS USA 84, 1839-1843, 1987).

Protein engineering techniques have allowed the availability of recombinant growth factors for therapeutic use. However, once they have been expressed these growth factors could be processed into a mixture of different forms. FGFs are no exception in this respect (Barr et al, J. Biol. Chem. 263, 31, 16471-16478, 1988).

We have now devised a process for the preparation of a bFGF which is truncated at its N-terminus. This process can be applied to obtain the 146-amino acid form of bFGF from longer forms and to produce a single form of bFGF from a mixture of bFGFs. The resulting form is pure and is not contaminated by other forms of bFGF.

Accordingly, the present invention provides a process for the preparation of a bFGF, which process comprises:

(i) forming an adduct between heparin or heparan sulphate and a bFGF which has the 9-10 Leu-Pro bond;
(ii) treating the adduct with pepsin A or cathepsin D, thereby cleaving the said bond; and
(iii) releasing from the adduct the bFGF thus obtained.

A mixture of two or more bFGFs which each have the 9-10 Leu-Pro bond, which have the same amino acid sequence from position 11 to their C-termini and which have different N-terminal amino acid sequences may be employed in step (i). Their amino acid sequences may differ only by having different N-termini. Typically, the only difference between the sequences of the bFGFs is that the number of N-terminal amino acid residues is different. One bFGF may have one or more additional N-terminal amino acid residues than another bFGF. Alternatively, the N-terminal amino acid sequences before position 9 of each bFGF may comprise different amino acid residues.

It is therefore possible to apply the present process to any mixture of bFGFs where the amino acid sequence of each bFGF in the mixture starts with a N-terminal amino acid residue numbered lower than 9 and the bFGFs have different N-termini. The mixture employed in step (i) may therefore be composed of bFGFs having the general formula:

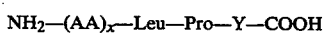

NH$_2$—(AA)$_x$—Leu—Pro—Y—COOH wherein AA is any amino acid residue, x is zero or an integer and Y denotes the amino acid sequence of (11-155)bFGF. Full length bFGF has 155 amino acid residues and can be designated 155-bFGF or (1-155)bFGF. The amino acid sequence of human (1-155)bFGF is shown in SEQ ID NO: 1. The invention can therefore be applied to one of, or a mixture of two or more of, (1-155)bFGF to (8-155)bFGF in which case x in the formula above is an integer of from 8 to 1 respectively and (AA)$_x$ denotes sequence shown one of SEQ ID NOS: 2 to 6, IleThrThr, ThrThr or Thr. In particular, the invention can be applied to a mixture of 154 amino acid residue bFGF[(2-155)bFGF] and 153 amino acid residues bFGF[(3-155)bFGF].

The bFGF or the mixture of bFGFs is generally obtained by recombinant DNA techniques. Different forms of bFGF are obtained in such mixtures due to processing of the translation product at its N-terminus. The or each bFGF may be a human, murine or rodent bFGF.

An adduct may be formed between a protecting agent for bFGF selected from heparin and heparan sulphate, and the mixture of bFGFs in any convenient fashion. The protecting agent and bFGFs are typically provided in an aqueous solution. This solution may be buffered. An antioxidant such as dithiothreitol may be present to prevent protein oxidation. The ratio of bFGF:protecting agent may be from 0.5:1 to 10:1 (w/w), for example from 1:1 to 5:1 (w/w). The protection of the bFGFs as adducts prevents further unwanted hydrolysis when pepsin A is added.

Pepsin A (EC 3.4.23.1) or cathepsin D (EC 3.4.23.5) is next contacted with the adduct. This results in specific cleavage of the 9-10 Leu-Pro bond in the bFGFs held in the adducts. The enzyme may be provided in a solution of the adduct. The enzyme may therefore be added to a solution of the bFGFs and the protecting agent. The enzyme is generally provided in a solution adjusted to pH 4 to 6.

The solution is incubated for, for example in the case of pepsin A, from 30 minutes to 10 hours, for example from 1 to 8 hours. Incubation is typically longer for cathepsin D, for example from 90 to 130 hours, suitably about 110 hours. The incubation temperature may be from 5° C. to room temperature, for example about 10° C. Incubation is carried out until reaction is complete.

Alternatively, the protecting agent may be immobilised on a support to form an affinity column. Any appropriate support may be used, such as an agarose gel or cross-linked dextran gel beads (for example Sepharose). A solution of the bFGFs is loaded onto the column. The bFGFs bind to the protecting agent and are held on the column. A solution of enzyme may then be passed through the column. Finally, the truncated single form of bFGF may be eluted from the column. This may be achieved with a linear gradient of aqueous sodium chloride solution.

A pure form of bFGF can be obtained by way of the present invention. In particular, the 146 amino acid form of bFGF designated (10-155) bFGF can be obtained. The bFGF obtained can be used to treat wounds and burns, for example. The bFGF may be applied to a wound or burn in any suitable formulation. Such formulations therefore typically further comprise a physiologically acceptable carrier or diluent.

The following Examples illustrate the invention. A Preparation Example and Comparative Examples are provided.

Preparation Example: Preparation of 154/153 form of bFGF

The construction of the synthetic DNA sequence for b-FGF and of the expression plasmid carrying such sequence was performed according to the procedure described in EP-A-363675. The fermentation and purification process was carried out as follows:

(a) Fermentation process

A bacterial strain, *E. coli* type B, from the Institute Pasteur collection, was transformed with a plasmid carrying both the human gene coding for bFGF and the gene for tetracycline resistance. This transformed strain was used for the production of recombinant nonglycosylated h-bFGF (human bFGF). A Master Cell Bank (15 freeze-dried vials) and a Working Cell Bank (W.C.B.) (70 vials stored in liquid nitrogen at $-190°$ C.) of this strain were prepared. The content of one vial of W.C.B. was used as the inoculum for the fermentation phase.

The fermentation process was carried out in 10 l fermentors filled with 4 l of culture medium. Tetracycline hydrochloride was added to the medium in order to maintain the conditions of strain selection. After 20 hours of growth at 37° C. the final biomass was $42\pm2$ g/l dry weight, and the production of bFGF was $2500\pm500$ mg/l as measured by comparative gel electrophoresis.

Enrichment in pure oxygen was required during the fermentation phase in order to allow a large bacterial growth.

(b) Initial purification

The cells (microorganisms) were separated from the total fermentation broth by centrifugation. The resulting pellet was resuspended in a sodium phosphate buffer containing sodium chloride. A minimum of 3 passages through a high pressure homogenizer were necessary for efficient cell breakage. The resulting cell lysate was clarified by centrifugation and the supernatant was collected for further processing.

(c) Purification

The clarified supernatant was loaded on a column of Sepharose (Trade Mark) S Fast Flow (cation exchanger) and the product was eluted from this column using a gradient of increasing sodium chloride concentrations in a phosphate buffer. The product was further purified on a column of Heparin Sepharose 6 B by eluting with a gradient of increasing sodium chloride concentration in a phosphate buffer. Finally a buffer exchange was made on a Sephadex (Trade Mark) G25 resin to obtain the product in the bulk product buffer (Sodium phosphate -EDTA).

(d) Column sanitization

Sepharose S Fast Flow and Sephadex G25 columns were sanitized by washing with sodium hydroxide solutions. Heparin Sepharose was washed alternatively with solutions at pH=8.5 and pH=5.5 containing 3M sodium chloride.

In this way, a 154/153 form of bFGF was obtained. This is an approximately 50:50 mixture of:
—a 154 amino acid human bFGF [(2-155)bFGF] having the amino acid sequence of the 155 amino acid form which is reported by Abraham et al and shown in SEQ ID NO: 1 but without the N-terminal Met residue; and
—a 153 amino acid human bFGF [(3-155)bFGF] consisting of the 155 amino acid form of bFGF shown in SEQ ID NO: 1 but without the N-terminal Met and Ala residues.

EXAMPLE 1: Heparan sulphate as protecting agent; pepsin A

1. Preparation of the protein sample

The 154/153 form of bFGF of the Preparation Example was provided at a concentration of 1.8 mg/ml in a buffered solution:
10 mM monosodium phosphate,
0.1 mM EDTA disodium salt,
pH 6.0.

To avoid any protein oxidation during the controlled hydrolysis, 20 mg of dithiothreitol were added to 1.8 mg of bFGF.

2. bFGF enzymatic hydrolysis procedure a) Standard solution of protecting agent Solution 1:
20 mg of protecting agent in 1 ml of $H_2O$
b) Preparation of solution of bFGF and protecting agent
100 μl of the protein sample,
9 μl of solution 1,
3 μl 1M sodium citrate, pH 3.0,
70 μl $H_2O$,
18 μg (18 μl) of pepsin A from porcine intestinal mucosa
Final volume: 200 μl The protecting agent was heparan sulphate and the bFGF/protecting agent ratio was 1:1 (w/w). Pepsin A (EC: 3.4.23.1) was added to the solution of bFGF and protecting agent at pH 4.0 and incubated at 10° C. for 1 hour.

3. Kinetics of the enzymatic hydrolysis

The hydrolysis procedure above was followed at different times by SDS-PAGE analysis. Samples of the digestion mixture were analysed after 1, 20, 40 and 60 minutes by SDS-PAGE. Separation of the 154/153 bFGF form from the 146-bFGF form was achieved in the SDS-PAGE analysis using the Phast System (Trade Mark; Pharmacia). With regard to the sample buffer, sample preparation conditions were defined as follows in order to avoid any protein precipitation of the sample in the stacking zone of the Phast Gel High Density:
15 μl of the protein solution,
10 μl of 40 mM Tris/HCl, 4 mM EDTA, 10% SDS, 20% mercaptoethanol, pH 8.0,
3 μl of DMSO (dimethyl sulphoxide), and
1 μl of Bromophenol blue (0.3%).

Sample denaturation was achieved by heating the sample at 100° C. for 5 minutes. The analysis of the samples showed that, in the sample taken from the digestion mixture after one hour, the 154/153-bFGF fragment had completely disappeared. One major fragment was obtained, which corresponded exactly to the 146-bFGF recombinant fragment used as reference.

4. Purification of bFGF

The reaction mixture was directly loaded onto a Heparin-agarose column preequilibrated with Tris buffer 10 mM, pH 8.0, 0.5M NaCl. bFGF was eluted at 1.5 M NaCl using a gradient of 0.5M to 3M NaCl. Protein concentration was determined by the Bradford method using 154/153 bFGF as reference.

5. Electroblotting of the 146-form bFGF

The procedure used in this electroblotting analysis was similar to that described by Ploug et al (Anal. Biochem. 181, 33-39, 1989). The membrane used was Immobilon PVDF (Millipore).

After electrophoresis, the gel was equilibrated in a transfer buffer (10 mM CAPS (3-[cyclohexylamino]-1-propanesulfonic acid), pH 11.0, 20% Methanol) for 10 min. The Immobilon PVDF was initially wetted with pure methanol and then equilibrated in the transfer buffer before use. A semi-dry blotting assembly was used (Kyhse-Andersen, J. Blochem. Biophys. Methods E, 10, 203-209, 1984). The electrotransfer was performed for 2 h at 0.2 mA/cm$^2$.

The PVDF membrane was rinsed in water and then stained in 0.1% (w/v) Coomassie brilliant blue R-250 in 50 % (v/v) methanol for 1 min. Excess dye was removed by a brief wash with water followed by destaining in 40% (v/v) methanol including 10% (v/v) acetic acid for 5-10 min. The PVDF membrane was then carefully rinsed in water before sequencing.

6. Amino-terminal sequence analysis

Cut areas of the PVDF membrane containing the stained protein were placed as a single layer on top of a Polybrene-conditioned filter. Sequencing was performed on an Applied Biosystems sequencer Model 470 A equipped with an on-line PTH-amino acid analyzer Model 120 A.

The first three amino acids of the NH$_2$-terminal part of the protein determined under these conditions were: Pro—Ala—Leu These amino acids correspond to the three amino acids of the amino-terminal 146-bFGF form.

7. Laser scan densitometry analysis

This analysis was carried out in order to determine the percentage of 146-bFGF produced after one hour of hydrolysis of 154/153-bFGF by pepsin A. After 1 h, 50 µl of the reaction mixture were mixed to 50 µl of SDS-denaturating buffer. In the same conditions, bFGF samples of different protein concentrations were SDS-denaturated. These samples were separated by electrophoresis on a gel PAA 4/30 (Pharmacia). The densitometry of each peak was analyzed using LKB BROMA 2220 recording integrator. Using the standard curve obtained in these conditions, it was found that the concentration of 146-bFGF form corresponded to 91% of the starting 154/153-bFGF concentration.

8. 146-bFGF yield after affinity purification

The yield of the enzymatic hydrolysis reaction was also determined after purification of the 146-bFGF form onto a heparin-agarose column. 1.64 mg of the reaction mixture from 2. above were loaded onto a heparin-agarose column preequilibrated with Tris 10 mM, pH 8, 0.5 M NaCl. At pH 8, pepsin A is not at all active and the complex between heparan sulfate and bFGF is destabilized, allowing the absorption of bFGF onto heparin-agarose present in excess in the medium. bFGF was eluted at 1.5 M NaCl. 1.14 mg of the 146-bFGF form was recovered.

The overall yield of the obtention of the 146-bFGF amino acid form after controlled hydrolysis using heparan sulfate as protecting agent and affinity column purification was 73%.

EXAMPLE 2: Heparin as protecting agent; pepsin A

The procedure of Example 1 was repeated except that the protecting agent was heparin, the bFGF-heparin ratio was 5:1 (w/w), aliquots of the digestion mixture were analysed after 2 minutes and 4, 6 and 8 hours and the total incubation time was 8 h. The solution of bFGF and heparin consisted of:

100 µl of the protein sample,
18 µl of solution 2,
3 µl of 1M sodium citrate, pH 3.0,
70 µl of H$_2$O,
18 µg of pepsin A,
final volume: 200 µl Solution 2 consisted of 100 l of solution 1 and 900 µl of H$_2$O. Under these conditions, only one fragment was also obtained after 8 hours incubation. This fragment had an apparent molecular weight of 16,200, as determined by SDS-PAGE analysis.

By amino-terminal sequence analysis, the same three N-terminal amino acids as in Example 1 were obtained: Pro—Ala—Leu

EXAMPLE 3: Heparin as protecting agent; pepsin A

The yield of the controlled hydrolysis of bFGF protected by heparin was also determined after purification of the 146-bFGF fragment onto a heparin-agarose column. After 7 h of hydrolysis in the same conditions as in Example 2, the reaction medium containing 1.54 mg of bFGF was loaded onto a heparin-agarose column preequilibrated with 10 mM sodium phosphate buffer, pH 8.0 and 0.5 M NaCl. 1.02 mg of 146-bFGF was eluted at 1.5 M NaCl.

The overall yield of the obtention of the 146-bFGF amino acid form after affinity column purification using heparin as protecting agent was 69%.

EXAMPLE 4-Heparin immobilized on Agarose as protecting AGENT; pepsin A

1. bFGF enzymatic hydrolysis procedure

A column of heparin-agarose (7 ml gel containing 5.6 mg of heparin) was equilibrated with sodium monophosphate 10 mM, 0.1 mM EDTA, NaCl 0.5 M, pH 4.0 at 10° C. The 154/153-bFGF was loaded on the affinity column. Then 0.18 mg of pepsin A diluted in the same phosphate solution was loaded on the top of the column. The enzyme is recirculated throughout the column at a 0.5 ml/min flow rate for 6 h.

At t=6 h, the column was washed with 10 mM sodium phosphate buffer pH 7.0, 0.1 mM EDTA, 0.5 M NaCl, (3 volumes), then with a 0.5M to 3M NaCl gradient. bFGF was eluted at 1.5 M NaCl.

2. Amino-terminal sequence analysis

After electrophoresis, the gel was electroblotted on Immobilon PVDF using a semi-dry blotting assembly as described in Example 1. Cut areas of the PVDF membrane containing the stained protein were placed as a single layer on top of a Polybrene-conditioned filter. The first three amino acid of the NH2-terminal part of the protein determined under these conditions were: Pro—Ala—Leu These amino acid correspond to the three amino acids of the amino-terminal part 146-bFGF form.

3. 146-bFGF recovery yield

The yield of the hydrolysis reaction was determined after the quantitative determination of the 146-bFGF fragment rinsed out of the heparin-agarose column. 1.28 mg of 146-bFGF was recovered. The overall yield of the obtention of the 146-bFGF amino acid form (Mw=16,200) after controlled hydrolysis onto a heparin-agarose column was 81%.

EXAMPLE 5: Heparin as protecting agent; cathepsin D

1. bFGF enzymatic hydrolysis procedure

Example 2 was repeated except cathepsin D from bovine spleen was used instead of pepsin A and the incubation time was 110 h.

2. Kinetics of the reaction

The appearance of the 146-bFGF fragment obtained during the enzymatic hydrolysis is very low but was detected by SDS-PAGE analysis after 1 h. After 72 h, the 154/153-bFGF hydrolysis was not complete and 36 µg of cathepsin D was added in the reaction medium. 40 h later, the reaction was complete. This is due to low activity of cathepsin D (10 units/mg).

3. Amino-terminal sequence analysis

After electrophoresis, the gel was electroblotted on Immobilon PVDF using a semi-dry blotting assembly as described in Example 1. Excised areas of the PVDF membrane containing the stained protein were placed as a single layer on top of a Polybrene-conditioned filter. Sequencing was performed on an Applied Biosystems sequencer analysis Model 470A equipped with an on-line PTH-amino acid analyzer Model 120A. The first three amino acid of the NH2-terminal part of the protein determined under these conditions were: Pro—Ala—Leu Comparative Example 1: Pepsin A without protecting agent Example 1 was repeated with the exception that no protecting agent was present. The 154/153 form of bFGF was completely digested by the pepsin A within a few minutes.

Comparative Example 2: Cathepsin D without protecting agent

Example 5 was repeated with the exception that no protecting agent was present. The 154/153 form of bFGF was completely digested by the cathepsin D within a few minutes.

Comparative Example 3; α-Chymotrypsin

Example 1 was repeated except that α-chymotrypsin was employed in place of pepsin A and no protecting agent was present. The 154/153 form of bFGF was completely digested by the α-chymotrypsin within a few minutes. Different anionic compounds were therefore tested for their ability to protect the bFGF from α-chymotrypsin:

1. Heparin 3,000 (Sigma, H 7516)

bFGF/protecting agent ratio =1
temperature=10° C.
pH=7.5
incubation time=4 h

Using heparin 3,000 as protecting agent, one fragment of apparent molecular weight of 14,000 was obtained mainly and some other fragments of lower molecular weight, as determined by SDS-PAGE analysis.

2. Heparin (Sigma, H 3135)

bFGF/protecting agent ratio (w/w)=5
temperature=10° C.
pH=7.5
incubation time=4 h Using this heparin grade as protecting agent, the protection was not suitable and many fragments were obtained.

3. Chondroitin sulfate bFGF/protecting agent ratio (w/w)=1
temperature=10° C.
pH=7.5
incubation time=2 h The protection was not suitable and many fragments were obtained.

4. Dermatan sulfate bFGF/protecting agent ratio (w/w)=1
temperature=10° C.
pH=7.5
incubation time=2 h The protection was not suitable and many fragments were obtained.

5. Polyaspartic acid bFGF/protecting agent ratio (w/w)=1
temperature=10° C.
pH=7.5
incubation time=2 h Using polyaspartic acid as protecting agent, the protection was not suitable and many fragments were obtained.

EXAMPLE 6: Heparin or heparan sulphate as protecting agent; pepsin A or cathepsin D

1. Experimental Protocol

Proteolytic treatment of soluble complexes bFGF-heparin and bFGF-heparin sulfate in solution 1.6 mg of the 154/153-amino acid form of bFGF were complexed to 1.6 mg of heparin or heparan sulfate in 10 mM citrate-phosphate buffer pH 4.0, 10° C. After 1 hour incubation time 160 µg of pepsin A (Sigma P-6887, 3200–4500 units/mg protein) were added to the solution. Samples of the reaction medium were taken at different times and directly loaded onto a heparin-Sepharose column preequilibrated with 10 mM phosphate buffer pH 8.0/0.5M NaCl at 4° C. The column was then washed extensively with the same buffer and the bFGF was eluted with 3 M NaCl in 10 mM phosphate buffer pH 8.0. The pooled fractions were desalted on a Sephadex G25 column previously equilibrated in 10 mM phosphate buffer pH 6.0 and subjected to the SDS-PAGE analysis. Using heparan sulfate as protective agent, 146-bFGF was obtained in quantitative yield after 1 hour. Pepsin treatment of bFGF-heparin complex led to the same quantitative yield just in 6.5 hours incubation time.

Pepsin A treatment of bFGF bound to a heparin-Sepharose column 50 mg of bFGF (154/153) were loaded at a flow rate of 2.5 ml/min on a heparin-Sepharose column (Pharmacia) (2.6×22.5 cm) previously equilibrated in 25 mM citrate buffer pH 4.0/0.5 M NaCl at 4° C. A solution of 680 units/ml of porcine pepsin A (Sigma) in citrate-phosphate buffer was continuously recycled through the column at 2.5 ml/min for 3 hours at 4° C. The column was then washed extensively with a 25 mM phosphate buffer pH 8.0/0.5 M NaCl to inactivate and to eliminate the enzyme. The bFGF was step-eluted with 3 M NaCl in 25 mM phosphate buffer pH 8.0. The bFGF-containing fractions were pooled, concentrated by ultrafiltration on Amicon PM 10 membrane and desalted on a Sephadex G25 column (Pharmacia) previously equilibrated in 10 mM phosphate buffer pH 6.0.
N-terminal sequence analysis Automated N-terminal sequence analysis was performed on a Model 477A Pulsed Liquid Phase Sequencer (Applied Biosystems, CA, USA) with on-line Model 120A PTH-Anlayzer. Normal-1 program with little modifications was used. All Sequencing materials and reagents were purchased from Applied Biosystems.
C-terminal sequence analysis Time-course study of carboxypeptidase P digestion of bFGF was performed at room temperature in 10 mM sodium acetate buffer pH 3.8/0.05% Brij-35, using an enzyme to substrate ratio of approximately 1:100 (w/w) (Lu et al, J. Chromatogr. 447, 351–364, 1988).

Digestions of 0.5–1 nmol of protein were carried out for two hours with 0.1–0.2 μg of CpP (Boehringer); N-Leucine was added as an internal standard. At different times 10/100 μl aliquots were withdrawn and subjected to amino acid analysis after automated derivatization with PITC on a Model 420A Derivatizer (Applied Biosystems) and subsequently injected into a RP-HPLC with on-line Model 130A analyzer. Separation of the derivatized PTC-amino acids was achieved on a PTC-C8 column (P/N 0711-0204, 220×2.1 mm, 5μ, Applied Biosystems).
Bioassays An endothelial cell-strain derived from bovine aorta (BAEC) was used to study the proliferative response induced by bFGF. Cells were plated at 2500 cells/well in 96 well microtitre plates in complete medium consisting of Dulbecco's Modified Eagle's Medium (DMEM) supplemented with 13% fetal bovine serum (FBS) (Gibco UK). After attachment, complete medium was replaced with experimental media consisting of DMEM supplemented with 0.5% fetal calf serum (FBS), 0.1% bovine serum albumin (BSA) (Sigma USA) and the desired concentrations of bFGF (Erbamont). The cultures were incubated for 3 days at which time they were fixed with formalin and stained with 0.5% crystal violet. After staining wells were thoroughly washed to remove unincorporated dye. Methanol (95%; 0.1 ml/well) was added to each well to extract the dye to an extent proportional to the amount of cells grown per well. Plates were transferred for automatic reading to a spectrophotometric microplate reader equipped with a 540 nm filter.

For the synthesis of plasminogen activator, BAEC ($3 \times 10^4$ cells in 0.2 ml/well) were seeded in 96 well microtitre plates in complete growth medium that was replaced after attachment with DMEM supplemented with 0.5% FBS, 0.1% BSA and the test concentrations of bFGF. After incubating for 28 h, cultures were washed and cells were lysed with a solution containing 0.5% Triton X-100. Aliquots of the cell-lysates were assayed for plasminogen activator activity using a chromogenic substrate (Spectrozyme PL) and plasminogen (both reagents from American Diagnostica Inc.) for the amidolytic assay.

2. Results

Controlled enzymatic Processing of bFGF

The purified recombinant 154/153 mixture was incubated with two different aspattic proteases: pepsin A and cathepsin D. Aliquots of the reaction mixture were taken at various time intervals and submitted to SDS-PAGE analysis showing that, in the absence of any protecting agent, bFGF was quickly digested into small peptides. On the contrary, the treatment of bFGF (154/153) with pepsin A (10:1 w/w; pH 4.0; 10° C.) in the presence of heparin or heparan sulfate (1:1 w/W), resulted in the progressive and complete conversion of the 154/153 amino acid forms to a lower molecular weight form which comigrated with our 146/145 amino acid form standard.

After electroblotting on a PDVF membrane the low molecular weight band that resulted from the enzymatic digestion was submitted to automated N-terminal sequence analysis on a pulsed liquid phase sequencer. The first three cycles resulted in a single homogeneous sequence; Pro-Ala-Leu that corresponds to the intact N-terminal end of the known 146-amino acid form. No other sequence was detected showing that, despite of the presence of three Leu-Pro sites on the bFGF molecule, when the-elongated forms of bFGF were complexed to heparin or to heparan sulfate, the digestion with pepsin A cleaved specifically and only the $Leu_9$-$Pro_{10}$ peptide bond.

A controlled proteolytic cleavage of the "heparin-protected" $NH_2$-extended bFGF molecule as obtained with pepsin A, was achieved after digestion with cathepsin D, although a longer incubation time was required for this proteolytic reaction, possibly due to the lower specific activity of the enzyme preparation used. When chymotrypsin was added under similar conditions but at pH 7.5, a single polypeptide of about 14000 dalton was detected after gel electrophoresis of the incubation mixture with no evidence of the presence of a 146 amino acid form.
Large scale enzymatic processing of bFGF on heparin-Sepharose column The results obtained in solution and in small batch reactions were verified on a larger scale process with the 154/153 mixture of elongated bFGF bound to a herparin-Sepharose column. Accordingly, 50 mg of bFGF (154/153) were loaded on a heparin-Sepharose column previously equilibrated in citrate-phosphate buffer pH 4.0. A solution of pepsin A was recycled continuously through the column for 3 hours at 4° C. Thereafter the column was washed with a phosphate buffer at alkaline pH both to inactivate and to eliminate the enzyme. The resulting polypeptide was eluted from the column with 3M NaCl in phosphate buffer at pH 8.0. The bFGF-containing fractions were collected and desalted on a Sephadex G25 column.

The pooled fractions analyzed on SDS-PAGE showed a single band with a molecular weight corresponding to that of the standard 146/145 bFGF form. Reverse-phase HPLC analysis resulted also in a single peak. N-terminal sequence analysis yielded a single sequence corresponding to the correct, intact N-terminal end of the 146-amino acid form, i.e. Pro-Ala-Leu-. C-terminal sequence analysis showed the expected carboxy-terminal end of the bFGF molecule, i.e. -Ala-Lys- Ser. Thus, also when bFGF was bound to the heparin-Sepharose resin, pepsin A was able to cleave specifically the molecule at the Leu$_9$-Pro$_{10}$ bond generating a homogeneous 146-amino acid form.

In vitro bioassays of the bFCF forms

The biological activity of the mixture of the 154/153-amino acid form was compared to that of the homogeneous 146-amino acid form obtained by the proteolytic process described. Two activities, the induction of a proliferative response and the synthesis of plasminogen activator, were studied in bovine aortic endothelial cells (BAEC). Both assays confirmed the in vitro biological equivalence of the 154/153- as compared to the 146-amino acid form obtained by the enzymatic process.

We claim:

---

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

( 2 ) INFORMATION FOR SEQ ID NO:2:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Met Ala Ala Gly Ser Ile Thr Thr
 1               5
```

( 2 ) INFORMATION FOR SEQ ID NO:3:

( i ) SEQUENCE CHARACTERISTICS:
( A ) LENGTH: 7 amino acids
( B ) TYPE: amino acid
( C ) STRANDEDNESS: single (D) TOPOLOGY: linear (ii) MOLECULE TYPE: peptide (xi) SEQUENCE DESCRIPTION: SEQ ID NO:3:

```
Ala Ala Gly Ser Ile Thr Thr
1               5
```

(2) INFORMATION FOR SEQ ID NO:4:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

```
Ala Gly Ser Ile Thr Thr
1           5
```

(2) INFORMATION FOR SEQ ID NO:5:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

```
Gly Ser Ile Thr Thr
1           5
```

(2) INFORMATION FOR SEQ ID NO:6:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

```
Ser Ile Thr Thr
1
```

1. A process for the preparation of a basic fibroblast growth factor (bFGF) having the formula $H_2N$-Pro-Y-COOH, wherein Y is the amino acid sequence of (11–155)bFGF as recited in SEQ ID NO:1, comprising:
   (i) forming an adduct between heparin or heparan sulphate and a bFGF having the formula $H_2N$-$(AA)_x$-Leu-Pro-Y-COOH, wherein $(AA)_x$ is a sequence selected from the group consisting of SEQ ID NO:2, SEQ ID NO:3, SEQ ID NO:4, SEQ ID NO:5, SEQ ID NO:6, Ile-Thr-Thr, Thr-Thr or Thr;
   (ii) treating the adduct with pepsin A or cathepsin D; and
   (iii) releasing said bFGF of the formula $H_2N$-Pro-Y-COOH from the adduct and recovering said bFGF of the formula $H_2N$-Pro-Y-COOH.

2. The process of claim 1, wherein said bFGF having the formula $H_2N$-$(AA)_x$-Leu-Pro-Y-COOH is a mixture of two or more of said bFGF's having the formula $H_2N$-$(AA)_x$-Leu-Pro-Y-COOH.

3. The process of claim 2, wherein said mixture is a mixture of said bFGF having the formula $H_2N$-(SEQ ID NO:3)-Leu-Pro-Y-COOH and said bFGF having the formula $H_2N$-(SEQ ID NO:4)-Leu-Pro-Y-COOH.

4. The process of claim 1, wherein said adduct is formed in a buffered aqueous solution, and said treating step comprises adding said pepsin A or said cathepsin D to said buffered aqueous solution containing said adduct.

5. The process of claim 1, wherein said heparin or said heparan sulfate is immobilized on a support to form an affinity column, said forming step comprises loading a solution of said bFGF of the formula $H_2N$-$(AA)_x$-Leu-Pro-Y-COOH onto said affinity column to form a loaded affinity column, said treating step comprises passing a solution of said pepsin A or said cathepsin D through the loaded affinity column, and said recovering step comprising eluting said bFGF of the formula H$_2$N-Pro-Y-COOH from said affinity column.

6. The process of claim 1, further comprising the step of admixing said bFGF of the formula H$_2$N-Pro-Y-COOH with a physiologically acceptable carrier or diluent.

7. The process of claim 1, wherein said bFGF having the formula H$_2$N-(AA)$_x$-Leu-Pro-Y-COOH and said heparin or said heparan sulfate are present in a ratio of from 0.5:1 to 10:1 by weight.

8. The process of claim 7, wherein said ratio is from 1:1 to 5:1.

9. The process of claim 1, wherein said treating step is conducted at a pH of from 4 to 6.

10. The process of claim 1, wherein said treating step comprises incubating said adduct with said pepsin A for a length of time of from 30 minutes to 10 hours.

11. The process of claim 10, wherein said length of time is from 1 to 8 hours.

12. The process of claim 1, wherein said treating step comprises incubating said adduct with said cathepsin D for a length of time of from 90 to 130 hours.

13. The process of claim 10 or 12, wherein said incubating is performed at a temperature of from 5° C. to room temperature.

14. The process of claim 13, wherein said temperature is from 5° C. to about 10° C.

15. The process of claim 14, wherein said temperature is 10° C.

* * * * *